(12) United States Patent
Eckard et al.

(10) Patent No.: US 6,225,267 B1
(45) Date of Patent: May 1, 2001

(54) SODIUM SULFONATE BLENDS AS EMULSIFIERS FOR PETROLEUM OILS

(75) Inventors: Alan Eckard, Chester, NY (US); Joseph A. Weaver, Jr., Powell; Igor Riff, Dublin, both of OH (US)

(73) Assignee: CK Witco Corporation, Greenwich, CT (US)

( * ) Notice: Subject to any disclaimer, the term of this patent is extended or adjusted under 35 U.S.C. 154(b) by 0 days.

(21) Appl. No.: 09/542,534

(22) Filed: Apr. 4, 2000

(51) Int. Cl.7 .................................................. C10M 135/10
(52) U.S. Cl. .......................... 508/390; 508/410; 508/412; 508/418
(58) Field of Search .................................. 508/390, 410, 508/412, 418

(56) References Cited

U.S. PATENT DOCUMENTS

| | | | |
|---|---|---|---|
| 1,930,488 | 10/1933 | Ramayya | 260/159 |
| 2,436,046 | 2/1948 | Lemmon et al. | 252/312 |
| 2,708,182 | 5/1955 | Jahn | 252/33 |
| 2,739,124 | 3/1956 | Otto et al. | 252/33 |
| 3,012,965 | 12/1961 | Sias | 252/33 |
| 3,367,865 * | 2/1968 | Gudelis | 508/390 |
| 3,406,115 | 10/1968 | White | 252/8.5 |
| 3,458,449 | 7/1969 | Mausner et al. | 252/182 |
| 3,753,904 * | 8/1973 | Holm | 508/390 |
| 3,769,209 * | 10/1973 | Holm | 508/390 |
| 4,062,957 | 12/1977 | Waldstein | 424/249 |
| 4,140,642 | 2/1979 | Kistler et al. | 252/33 |
| 4,176,076 | 11/1979 | Waldstein | 252/49.6 |
| 4,753,754 * | 6/1988 | Messenger et al. | 508/390 |
| 4,778,614 * | 10/1988 | Rawlinson et al. | 508/390 |
| 4,873,025 | 10/1989 | Bolsman | 562/91 |
| 5,298,177 | 3/1994 | Stoffa | 252/18 |
| 5,322,631 | 6/1994 | Fuchigami et al. | 252/33.2 |
| 5,427,700 | 6/1995 | Stoffa | 252/18 |
| 5,929,003 * | 7/1999 | De Montlaur | 508/390 |
| B1 4,753,754 * | 5/1997 | Messenger et al. | 510/424 |

* cited by examiner

Primary Examiner—Jacqueline V. Howard
(74) Attorney, Agent, or Firm—Daniel Reitenbach

(57) ABSTRACT

The present invention relates to an emulsifier composition suitable for mixing with oil to form lubricants comprising at least one non-extracted salt of a natural petroleum sulfonic acid having about 15 wt-% to about 30 wt-% active content; at least one branched chain alkylaryl sulfonic acid or salt thereof; at least one linear alkylaryl sulfonic acid or salt thereof; and optionally at least one other sulfonic acid or salt thereof for adjusting the average equivalent equivalent weight of the resultant emulsifier composition.

26 Claims, No Drawings

SODIUM SULFONATE BLENDS AS EMULSIFIERS FOR PETROLEUM OILS

FIELD OF THE INVENTION

The present invention relates to an emulsifier composition comprising at least one natural petroleum sulfonic acid salt produced by treating petroleum oil with oleum or sulfur trioxide, at least one branched chain alkylaryl sulfonic acid salt, at least one linear alkylaryl sulfonic acid salt, and at least one other optional sulfonic acid salt that may be used to adjust equivalent weight. This combination provides a system with good oil compatibility and optimum emulsion performance.

BACKGROUND OF THE INVENTION

Sodium petroleum sulfonates are widely used as the primary emulsifier in formulating emulsifiable lubricating compositions used for cutting fluid, hydraulic fluids, metalworking lubricants, and so forth.

Sodium petroleum sulfonates are typically produced as a by-product of refining processes in which certain highly refined petroleum products such as white lubricating oils, medicinal oils, and certain grades of transformer oils, are produced. The highly refined petroleum products are produced by treating a refined petroleum distillate or raffinate with fuming sulfuric acid which reacts with certain components of the oil to produce sulfonic acids, some of which are oil-soluble and some of which are water-soluble, thus forming a two-phase system. The two phases separate into two layers one of which is the oil layer containing the oil-soluble reddish-brown or mahogany sulfonic acids, and one of which is the water-soluble layer commonly referred to as an acid sludge layer that contains resinous materials, unreacted sulfuric acid, and water-soluble or green sulfonic acids. The layers are then separated and the oil-soluble sulfonic acids are recovered from the oil layer, usually in the form of their sodium salts.

The mahogany sulfonic acids being preferentially oil-soluble have found wide use in the preparation of emulsifiable petroleum products, such as in soluble cutting oils, hydraulic fluids, metalworking lubricating fluids for forming of metals, and so forth. The acid oil layer is neutralized to make a sodium salt and extracted with a polar solvent, typically alcohol, to separate most of the oil phase, and to increase the activity of the sodium sulfonate. This type of process is discussed generally in U.S. Pat. No. 1,930,488. The manufacture of white oils by the above process has become increasingly uneconomical and as a result, the production of sulfonates as by-products of white oil refining is substantially declining. This has left a significant shortage of sodium petroleum sulfonates.

Another major disadvantage with the natural petroleum sulfonates is their inconsistency in quality, and hence a variance in their emulsifying properties. In order to improve emulsification properties, secondary surface active agents of different types are often added, for instance, fatty acid salts. The amount of the secondary surface active agent used is varied depending on the quality of the sulfonate being employed. U.S. Pat. No. 4,140,642 describes an improved emulsifier composition in which salts of alkylaryl sulfonic acids are employed with an organic or mineral base, and in which the equivalent weights of the acids are distributed according to a function of $C=f(M)$ where C denotes the concentration and M denotes the equivalent weight of individual acids, which function has two distinct equivalent weight maximum $M_1$ and $M_2$, with $M_1<M_2$. Surprisingly, the present inventors have found a blend of sulfonates that provides an emulsifier composition that has consistent emulsification properties, and that is economical as well. This blend comprises at least one natural alkali metal petroleum sulfonate that is not prepared as a by-product of an oil refining process and may be non-extracted, and a blend of other high active synthetic sulfonates or sulfonic acids selected so as to produce an emulsification system that has 60% or greater active content, and selected so as to balance the oil solubility and emulsification performance thus providing an excellent surfactant system.

SUMMARY OF THE INVENTION

The emulsifier blend according to the invention comprise a blend of sulfonates or sulfonic acids that may be neutralized to the salt form, the blend comprising at least one natural sodium petroleum sulfonate that is derived from a typical lube base oil of 15–400 Cst viscosity at 40° C., and preferably is a non-extracted sodium petroleum sulfonate, at least one branched alkylaryl sulfonate, at least one linear alkylaryl sulfonate, and optionally, at least one other sulfonic acid or salt that preferably has an active content of 60% or greater. Any of these compounds may be supplied either in salt or in acid form. Optionally, other extracted petroleum sulfonates may also be added to the compositions of the present invention. The branched sulfonate is preferably an alkylbenzene and the linear sulfonate is preferably an alkylxylene.

The optional sulfonic acid or salt may be selected from a group of compounds including low, medium, high and very high equivalent weight sodium petroleum sulfonates; low, medium and high equivalent weight synthetic sodium sulfonates; low, medium and high equivalent weight sulfonic acids; high equivalent weight branched and linear alkylbenzene sulfonic acids where the side chain is $C_8$ to $C_{30}$; and $C_{10}$ to $C_4$ sulfonated alkylation bottoms as sodium salts. The natural sulfonic acid salts of the present invention are prepared by oleum or $SO_3$ sulfonation of the aromatics contained in a typical lube base oil of 15–400 cSt viscosity at 40° C. The acid oil is desludged by gravity settling and neutralized with any monovalent cation from a base, preferably sodium. The sulfonate is not extracted or solvent treated to remove oil or salts. The process is thus simplified over previously used processes for preparing natural petroleum sulfonic acid salts for use in emulsifier compositions. The present invention further relates to a method of preparing an emulsifier composition suitable for mixing with oil to form lubricants comprising the steps of preparing a non-extracted natural petroleum sulfonate comprising the steps of providing a petroleum oil; adding fuming sulfuric acid or sulfonating agent to the petroleum oil; desludging the petroleum oil; and neutralizing the petroleum oil. This process is simplified and more economical than previous manufacturing procedures in that no extraction step is required. At least one branched chain alkylaryl sulfonic acid or salt thereof and at least one linear alkylaryl sulfonic acid or salt thereof is then added to the non-extracted natural petroleum sulfonate. Optionally, one or more sulfonic acids or salt thereof derived from alkylation bottoms may be added to the mix. All remaining sulfonic acid is then neutralized with one or more monovalent cation bases such as NaOH to form a neutral salt.

This sulfonate salt mixture may then be added to a mineral oil such as a naphthenic or paraffinic oil as a primary emulsifier to make cutting fluid concentrate for metalworking. Additional co-emulsifiers and lubricity additives may be usefully included as well. The cutting fluid concentrate is then added to aqueous media forming an emulsion that is useable as a metalworking lubricant. The term "cutting fluid" refers to the use of both emulsions and oils.

DETAILED DESCRIPTIONS OF THE PREFERRED EMBODIMENTS

The first component of the inventive composition are natural petroleum sulfonates or sulfonic acid salts prepared using sulfuric acid, oleum, (i.e. fuming sulfuric acid) and/or sulfur trioxide or other sulfonating agent to sulfonate petroleum oil, preferably a paraffinic oil. A preferred oil for use herein is a typical lube base oil of 15–4000 cSt @ 40° C. The acid oil is desludged by settling using natural gravitational forces, and is subsequently neutralized to about a 15–30%, preferably about 20–30% active petroleum sulfonate in oil. No further extraction or processing for the removal of oil or salts is conducted. These sulfonates will be hereinafter referred to as non-extracted sulfonates to distinguish them from the natural sulfonates that are prepared as a by-product of a refining process. These non-extracted natural sulfonates, as neutral salts, provide corrosion protection properties to metal, and assist in emulsification performance. Other extracted sulfonates may be added to the present invention in combination with the non-extracted sulfonates of the present invention. The petroleum sulfonates used as the first component of the present invention are very economical to produce due to the minimum amount of processing required. The preferred paraffinic oil feed stream is low cost and in abundant supply. The sulfonates can be blended with other sulfonate emulsifiers to produce a product of preferably 60% or greater active content, for instance with highly active sulfonic acids. An example of a natural sodium petroleum sulfonate of this type is Sodium petroleum sulfonate, MNT, a 30% active sulfonic acid salt supplied by CK Witco in Greenwich, Conn. In the previous method of preparing concentrated petroleum sulfonate emulsifiers, a separation/extraction process is used to prepare the final product. Using these methods, oleum or sulfur trioxide is added to the petroleum oil to remove the aromatics, and to produce USP white oils or special naphthenic process oils. After the acid treatment, the spent acid and low equivalent weight sulfonic acids, i.e. sludge acids, are separated from the oil soluble acids. The later material is then neutralized to make a sodium salt and is extracted with a polar solvent(s), typically lower alcohols, to separate most of the oil and increase the activity of the sodium sulfonate. This process, however, is becoming economically unfavorable as alternative sources of white oil become available. The present invention, in contrast, does not separate oil from the sulfonic acid and requires no extraction.

The sulfonic acid salts may be either inorganic or organic. The preferred inorganic salts are sodium salts. However, ammonium salts, or those of the other alkali metals, or the alkaline earth metals are possible as well. Inorganic compounds include, but are not limited to, barium, calcium, lithium, rubidium, cesium, magnesium, potassium, sodium, strontium, radium, zinc, iron, copper, aluminum, and so forth, with sodium being the preferred metal for use herein. The organic bases which may be employed are nitrogen bases, for example a primary, secondary or tertiary amnine, a polyamine, an alkanolamine including monoethanolamine, diethanolamine, triethanolamine and mixtures thereof.

The preferably non-extracted, natural sulfonates so produced are usefully employed in the inventive compositions in amounts from about 10 wt-% to about 70 wt-%, preferably about 20 wt-% to about 60 wt-% of the total emulsifier composition, and more preferably from about 30 wt-% to about 50 wt-% of the total composition.

The high active sulfonates for use in combination with the natural petroleum sulfonates of the present invention are carefully selected so as to balance the oil compatibility, and the emulsification performance of the resultant emulsifier blend. According to the present invention, the sulfonates of the present invention are blended with the other more highly active sulfonates as described in detail below.

The emulsifier compositions of the present invention also comprise, as a second component, at least one branched alkylaryl sulfonate. These branched structures have been known to exhibit improved solubility and emulsion stability. Branched chain alkylaryl sulfonates are discussed in U.S. Pat. No. 4,140,642 incorporated herein by reference in its entirety. Aryl groups include benzene, toluene, naphthalene, xylene, and so forth. In a preferred embodiment of the present invention, tetrapropenatedbenzene sulfonate is utilized. Substituting a linear alkylaryl sulfonate for the branched chain structure decreases the solubility and overall emulsion stability. This results in haziness and possible occurrence of separation in the soluble oil concentrate.

The branched chain alkylaryl sulfonate is suitably employed in an amount from about 5 wt-% to about 40 wt-%, preferably from about 10 wt-% to about 30 wt-% of the total composition, more preferably about 10 wt-% to about 20 wt-%, and most preferably about 11–14% (95% active). A specific branched alkylaryl sulfonate is WITCO® 1298H, a $C_{12}$ benzene sulfonic acid supplied by CK Witco Corp. The branched sulfonic acids may be a $C_8$ to $C_{30}$ alkyl, preferably $C_8$ to $C_{24}$ and more preferably $C_{10}$ to $C_{24}$ alkyl.

The third component of the inventive composition is a linear alkylaryl sulfonate, preferably a linear alkylxylene sulfonate. Again, suitable aryl groups include benzene, toluene, xylene, naphthalene, and so forth.

The linear chain alkylaryl sulfonates can be used preferably in amounts of about 5 to about 50 wt-% of the total active sulfonates, preferably from about 10 wt-% to about 50 wt-%, and more preferably from about 20 to about 30 wt-%. These sulfonates are from $C_8$ to $C_{30}$ alkyl, preferably $C_8$ to $C_{24}$, and most preferably from about $C_{10}$ to $C_{24}$ alkyl. A specific preferred linear alkylaryl sulfonate is an alkyxylene sulfonate, more specifically monoalkylxylene sulfonate, and in particular is dodecylxylene sodium sulfonate, a high active content (about 70 wt-% in salt form) sodium sulfonate. This material may also be supplied in an unneutralized acid form (90–95 wt-% active content).These linear alkylaryl sulfonates contribute the attributes of a low equivalent weight component while maintaining complete solubility in oil. These materials are preferable because they are registered for use on both the TSCA and the DSL inventories. An example of such a material is L-DDX supplied by CK Witco Corp. in Greenwich, Conn.

These alkylaryl sulfonates, both branched and linear, may be prepared using standard sulfonation techniques which typically involve sulfonation of the appropriate of aromatic hydrocarbons, thereby obtaining the alkylaryl sulfonic acids which are then subsequently neutralized with a base.

The alkylation may be carried out using any method known to one of skill in the art including a Friedel-Crafts reaction using an alkyl halide, alkanol, or alkene reactant in the presence of a Lewis acid catalyst. Catalysts may include hydrogen fluoride and activated clay.

The sulfonation is then carried out typically by contacting the alkylated aromatic compound with concentrated sulfuric acid and/or sulfur trioxide ($SO_3$). The sulfonic acid may then be neutralized with a base, although as noted above, the compounds can be supplied in either acid or salt form.

The compositions of the present invention may optionally further comprise other alkylaryl sulfonates or sulfonic acid salts selected from a wide variety of high active natural and synthetic sulfonic acids or salts including medium, high and very high equivalent weight sodium petroleum sulfonic acids and salts thereof; low, medium and high equivalent weight synthetic sodium sulfonic acids or salts thereof such as ARISTONATE® L, M and H (salt form) and ARISTONIC® L, M and H (acid form); high equivalent weight branched and linear alkylbenzene sulfonic acids and salts thereof where the side chain is $C_{14}$ to $C_{30}$; and the sodium salts of sulfonated $C_{10}$ to $C_{14}$ alkylation bottoms. The bottoms material is manufactured starting from an alkylate. The alkylate is typically produced as a product of an alkylation process and may be referred to as an alkylation bottoms, a distillation residue from the alkylation process. One such process from which this by-product material may be produced is from the dodecylation of benzene. Dodecyl benzene is distilled off and the alkylates remaining may be used to produce the sodium sulfonates of the present invention. The alkylate is sulfonated to a high purity sulfonic acid which is subsequently neutralized with an alkali metal hydroxide, for instance sodium hydroxide, to the salt form. These compounds are useful in adjusting the equivalent weight or other performance parameters. The objective is to replace a natural petroleum sulfonate that is prepared in the standard way, i.e. as a by-product of the white oil refining process, which includes and extraction process, with a blend of sulfonates in order to achieve the same performance. For instance, these compounds may be used to adjust the equivalent weight of the total emulsifier composition to a low equivalent equivalent weight of about 400 g/mole, or to adjust it to a high equivalent equivalent weight of about 500 g/mole. Materials having a equivalent weight of less than about 400 are typically not sufficiently oil soluble for such applications. Materials having an equivalent weight of greater than about 500 g/mole, while exhibiting good corrosion protection properties, typically exhibit poor emulsion performance.

Petroleum sulfonates classified as low (L) equivalent weight petroleum sulfonates typically have a equivalent weight of about 410–440 g/mole, while those classified as medium (HL; referred to in this fashion because it was typically supplied as a blend of low and high equivalent weight petroleum sulfonates) equivalent weight petroleum sulfonates typically have a equivalent weight of about 450–480 g/mole and those classified as high (H) equivalent weight petroleum sulfonates typically have a equivalent weight of about 490–520 g/mole.

These general equivalent weight ranges apply to both synthetic and natural petroleum sulfonates, and work well for a range of metalworking applications. Preferably, the sulfonates have an active content of about 60% or more, and up to about 95% active content.

These sulfonates are useful from up to about 20 wt-% of the total fluid concentrate, and preferably from about 5 wt-% to about 15 wt-% of the total composition. A specific example of a useful sulfonate is Petronate HL, a 62% active sodium petroleum sulfonate.

A specific example of a preferred composition for replacing a medium equivalent weight alkali metal petroleum sulfonate, prepared by the standard process, i.e. a by-product of petroleum refining in which acid sludge and oil soluble fractions are separated and the salt extracted to increase active content to 60% minimum, is about 40% to about 50% by weight of at least one petroleum sulfonic acid in petroleum oil (about 30% active) prepared by the method of the present invention, i.e. no extraction; about 11% to about 14% by weight of at least one branched alkyl benzene sulfonic acid (about 95% active or more); about 22% to about 25% by weight of at least one linear alkylxylene sulfonic acid (90–95% active); and about 8% to about 14% by weight of at least one $C_{14}$ to $C_{30}$ synthetic sulfonic acid (about 90% active) such as a $C_{14}$ to $C_{30}$ dialkyl benzene, a $C_{14}$ to $C_{30}$ alkyl benzene, a $C_{14}$ to $C_{30}$ alkyl toluene, or a $C_{14}$ to $C_{30}$ alkyl naphthalene, for instance. One consideration in selecting the preferred emulsifiers was the compliance with current regulatory restrictions in North America, including TSCA and DSL. The various alkylates and oil used to produce the sulfonate having the desired equivalent weight can be blended together prior to sulfonation, thus streamlining the sulfonation and neutralization processes.

The components of the present invention are selected so as to produce a composition of emulsifiers that is completely soluble in petroleum or refined petroleum oils. Preferably a paraffinic petroleum oil is used. For instance, a white mineral oil may be chosen such as Carnation® White mineral oil available from CK Witco Corp. in Greenwich, Conn.

The emulsifier composition of the present invention may be added to a petroleum oil in an amount of about 10 wt-% to about 50 wt-% of the total mixture which resultant oil based composition may be used as a cutting fluid for metalworking, for instance. For such applications, it is desirable that the petroleum oil, paraffinic or naphthenic, used have a viscosity from about 5 to about 100 cSt at 40° C. These petroleum oils, in addition to the emulsifier composition of the present invention, may comprise from about 0 wt-% to about 10 wt % fatty acid soap, 1 wt-% to about 10 wt-% of one or more extreme pressure lubricating agents, from about 0.1 wt-% to about 5 wt-% of one or more other anti-corrosion agents; from 0.1 wt-% to about 3 wt-% of one or more bactericidal agents. One of skill in the lubricant art would have knowledge of the additional agents that may be added to the fluid. The cutting fluid concentrate is then dispersed in water, producing a stable aqueous emulsion for metalworking.

The compositions of the present invention also find use in other petroleum oil based compositions, particular those used for industrial applications, such as hydraulic fluids, grinding fluids, rust preventative fluids, drawing fluids, rolling fluids, oil-in-water and water-in-oil emulsions, and so forth.

The following non-limiting examples further illustrate the present invention.

EXAMPLES

Example 1

A concentrate of mixed sulfonates was prepared according to the invention by mixing 16 wt-% WITCONATE® 1298H, a $C_{12}$ branched chain alkyl benzene sulfonic acid, 96% active; 25 wt-% L-DDX, a $C_{12}$ linear orthoxylene sulfonic acid, 90% active; 14 wt-% ARISTONIC® H, a $C_{15}$–$C_{30}$ alkyl benzene sulfonic acid comprised of mono- and dialkyl groups; and 41 wt-% petroleum sulfonic acid in petroleum oil, i.e. acid-oil, with a 15–40% concentration of sulfonic acid (may be referred to as approximately 30% active) derived by sulfonation of a petroleum fraction. This acid-oil has a viscosity of 100 to 130 cSt at 400° C.

The acid-oil may then be neutralized with sodium hydroxide. The final composition after neutralization with sodium hydroxide was 62% active sodium sulfonate with an average equivalent weight of 450 g/mole. This composition is particularly useful for metalworking fluids that provide emulsification, lubrication and rust protection.

Example 2

A concentrate of mixed sulfonates was prepared according to the invention by mixing 16 wt-% WITCONATE® 1298H, $C_{12}$ branched chain alkyl benzene sulfonate; 25 wt-% L-DDX, $C_{12}$ linear orthoxylene sulfonic acid; 16 wt-% ARISTONIC® H, synthetic $C_{15}$–$C_{30}$ alkylbenzene sulfonic acid comprised of mono- and dialkyl groups; and 39 wt-% of a natural petroleum sulfonic acid in petroleum oil, i.e. acid oil, 15–40% concentrate (typically referred to as approximately 30% active) derived by sulfonation of petroleum fraction. The acid-oil has a viscosity of 100 to 130 cSt at 40° C. The final composition after neutralization was 62% active sodium sulfonate with an average equivalent weight of 425 g/mole. This composition can be utilized as a blend with high equivalent weight sulfonate salts to formulate metalworking fluids providing emulsification, lubrication and rust protection.

Comparative Example A

A concentrate of mixed sulfonates was prepared by mixing 10 wt-% WITCONATE® 1298H, $C_{12}$ branched alkylbenzene sulfonic acid, 96% active; 24 wt-% L-DDX, $C_{12}$ linear orthoxylene sulfonic acid, 90% active; 17 wt-% ARISTONIC® H, a $C_{15}$–$C_{30}$ alkylbenzene sulfonic acid comprised of mono- and dialkyl groups, 90% active; and 52 wt-% sodium petroleum sulfonate derived by sulfonation of petroleum fraction with a viscosity of 100 to 130 cSt @ 40° C., 30% active. The final composition after neutralization had a equivalent weight of about 500 g/mole, and exhibited weaker emulsification properties. The example reflects the effect on the emulsification inherent in higher equivalent weight sodium sulfonates. An emulsion of example A provided excellent corrosion protection when tested according to ASTM D-4627 and was significantly better than examples 1 and 2 above.

We claim:

1. An emulsifier composition suitable for mixing with oil to make lubricants, comprising:
   a) at least one non-extracted natural petroleum sulfonic acid or salt thereof having about 15 wt-% to about 30 wt-% active sulfonate;
   b) at least one branched chain alkylaryl sulfonic acid or salt thereof; and
   c) at least one linear alkylaryl sulfonic acid or salt thereof.

2. The composition of claim 1 wherein said salts are selected from the group consisting of organic and inorganic cations.

3. The composition of claim 2 wherein said salts are selected from the group consisting of amines, polyamines, alkanolamines, ammonium, barium, calcium, lithium, magnesium, potassium, sodium, strontium, zinc, iron, copper and aluminum.

4. The composition of claim 2 wherein said salts are sodium or potassium salts.

5. The composition of claim 1 wherein said branched chain alkylaryl sulfonic acid or salt is a $C_8$ to $C_{30}$ alkylbenzene sulfonic acid or salt.

6. The composition of claim 1 wherein said branched chain alkylaryl sulfonic acid is an alkylation product of benzene and olefin, olefin oligomer, or mixture thereof.

7. The composition of claim 6 wherein said olefin is polypropylene.

8. The composition of claim 6 wherein said olefin is polyisobutylene.

9. The composition of claim 1 wherein said linear alkylaryl sulfonic acid is alkylated with dodecene and said aryl portion is xylene.

10. The composition of claim 1 further comprising at least one equivalent weight adjusting compound for adjusting the average sulfonate equivalent weight of the total composition, said equivalent weight adjusting compound selected from the group consisting of medium, high and very high equivalent weight sodium petroleum sulfonic acids and salts thereof; low, medium and high synthetic sodium sulfonic acids and salts thereof; synthetic high equivalent weight $C_8$ to $C_{30}$ branched chain alkylaryl sulfonic acids or salts; synthetic high equivalent weight $C_8$ to $C_{30}$ linear alkylaryl sulfonic acids and salts thereof; sodium salts of sulfonated $C_{10}$ to $C_{14}$ alkyl alkylation bottoms; and mixtures thereof.

11. The composition of claim 10 wherein said compound is selected from the group consisting of synthetic high equivalent weight $C_{14}$–$C_{30}$ branched alkylaryl sulfonic acid, $C_{14}$–$C_{30}$ linear alkylaryl sulfonic acids, and mixtures thereof.

12. The composition of claim 10 wherein said compound comprises a mixture of compounds selected from the group consisting of alkylbenzene sulfonic acids, dialkylbenzene sulfonic acids, alkyltoluenes, alkyl naphthalenes and mixtures thereof.

13. The composition of claim 10 wherein said average sulfonate equivalent weight of said total emulsifier composition is about 400 to about 500 g/mole.

14. The composition of claim 10 wherein said equivalent weight adjusting compound has an active sulfonate content from about 40% to about 95% by weight of said compound.

15. The composition of claim 1 wherein said branched chain alkylbenzene sulfonic acid or salt thereof has an active content of about 50 wt-% or greater.

16. The composition of claim 1 wherein said linear alkylaryl sulfonic acid or salt thereof has an active content of about 50% or greater.

17. The composition of claim 1 wherein said composition has an active sulfonate content of about 40% to about 90%.

18. The composition of claim 1 comprising from about 10 wt-% to about 60 wt-% of a); about 5 wt-% to about 40 wt-% of b); and about 5 wt-% to about 50 wt-% of c).

19. The composition of claim 18 further comprising up to about 40 wt-% of an equivalent weight adjusting compound for adjusting the average sulfonate equivalent weight of the resultant composition, said equivalent weight adjusting compound selected from the group consisting of medium, high and very high equivalent weight sodium petroleum sulfonic acids and salts thereof; low, medium and high synthetic sodium sulfonic acids and salts thereof; synthetic high equivalent weight $C_{14}$ to $C_{30}$ branched alkylaryl sulfonic acids or salts thereof; synthetic high equivalent weight $C_{14}$ to $C_{30}$ linear alkylaryl sulfonic acids and salts thereof; sodium salts of sulfonated $C_{10}$ to $C_{14}$ alkyl alkylation bottoms; and mixtures thereof.

20. A lubricating or cutting fluid composition comprising a composition as in claim 1 and oil or oils selected from the group consisting of paraffinic and naphthenic petroleum oil and paraffinic and naphthenic refined petroleum oil in an amount about 50 wt-% to about 95 wt-% of the total oil based composition.

21. An aqueous emulsion prepared by dispersing a composition as in claim 1 dispersed in aqueous media.

22. An emulsifier composition suitable for mixing with oil to form lubricants comprising:
   a) at least one non-extracted petroleum sulfonic acid or salt thereof having a active content of about 15 wt-% to about 30 wt-%;

b) at least one branched chain alkylaryl sulfonic acid or salt thereof;

c) at least one linear alkylaryl sulfonic acid or salt thereof; and d) at least one compound selected from the group consisting of medium, high and very high equivalent weight sodium petroleum sulfonic acids and salts thereof; low, medium and high synthetic sodium sulfonic acids and salts thereof; synthetic high equivalent weight $C_{14}$ to $C_{30}$ branched alkylaryl sulfonic acids or salts thereof having a side chain of; synthetic high equivalent weight $C_{14}$ to $C_{30}$ linear alkylaryl sulfonic acids and salts thereof; sodium salts of sulfonated $C_{10}$ to $C_{14}$ alkyl alkylation bottoms; and mixtures thereof.

23. The composition of claim 22 wherein said branched chain alkylaryl sulfonic acid or salt thereof is an alkylbenzene sulfonic acid or salt thereof.

24. The composition of claim 22 wherein said linear chain alkylaryl sulfonic acid or salt thereof is an alkylxylene sulfonic acid or salt thereof.

25. The composition of claim 1 wherein said nonextracted petroleum sulfonic acid or salt thereof is a desludged sulfonate of a lube base oil of 70–700 SUS (15–150 cSt @ 40° C.) viscosity at 1000° F. (37.8° C.).

26. The composition of claim 1 wherein said nonextracted petroleum sulfonic acid or salt thereof is a sludge free sulfonate of a lube base oil of 15–400 cSt viscosity @ 40° C.

* * * * *